United States Patent [19]

Eskilsson

[11] Patent Number: 5,013,868

[45] Date of Patent: May 7, 1991

[54] PROCESS FOR TREATING AMPHOTERIC AMINO ACIDS

[75] Inventor: Eva C. Eskilsson, Mölnlycke, Sweden

[73] Assignee: Lejus Medical Aktiebolag, Molndal, Sweden

[21] Appl. No.: 143,392

[22] Filed: Jan. 13, 1988

[30] Foreign Application Priority Data

Jan. 15, 1987 [SE] Sweden ............................ 8700136

[51] Int. Cl.$^5$ ............................................ C07C 321/00
[52] U.S. Cl. ................................. 562/557; 562/446
[58] Field of Search ............................. 562/557, 446

[56] References Cited

U.S. PATENT DOCUMENTS

| | | | |
|---|---|---|---|
| 4,102,806 | 7/1978 | Kondo | 252/316 |
| 4,218,435 | 8/1980 | Shiba | 424/72 |
| 4,394,520 | 7/1983 | Kulopissis | 562/557 |
| 4,732,765 | 3/1988 | Sasagawa | 424/476 |

FOREIGN PATENT DOCUMENTS 1002889 9/1965 United Kingdom.

*Primary Examiner*—Michael L. Shippen
*Attorney, Agent, or Firm*—Burns, Doane, Swecker & Mathis

[57] ABSTRACT

The present invention relates to a process for treating amphoteric amino acids, and/or amphoteric amino acid derivatives in a fluid bed, whereby in order to maintain fluidizing conditions one adds at least 0.2% by weight of a fatty acid, fatty alcohol and/or fat, preferably containing 14°-20° C.

17 Claims, No Drawings

PROCESS FOR TREATING AMPHOTERIC AMINO ACIDS

DESCRIPTION

TECHNICAL FIELD

The present invention relates to a process for treating amphoteric amino acids, particularly in connection with the utilization of fluid bed.

The object of the present invention is to obtain a possibility to treat amphoteric amino acids in a fluidized bed while maintaining fluidization.

BACKGROUND OF THE INVENTION

Modern foodstuff and pharmaceutical technology utilizes to an ever increasing extent the fluid bed technique for treating different materials. The fluid bed technique thereby provides for a treatment of single particles of compounds in different ways, such as coating, drying etc.

It has, however, turned out that, when introducing pure amphoteric amino acids, or derivatives of amino acids in a fluid bed, as well as in such cases when such an amino acid or derivative thereof is a substantial part of a composition (80 to 90% amino acid) the fluidization ceases after a very short time following the starting up. The whole mass of product thereby cakes together and settles along the bottom and sides of the apparatus.

This is an evident drawback, particularly as one in many cases wants to work with substantially pure compositions of amino acids. It has thus turned out a need for solving this problem which, if unsolved, makes any use of a fluid bed impossible for such amphoteric amino acids or derivatives thereof.

DESCRIPTION OF THE PRESENT INVENTION

It has now surprisingly been shown possible to solve said problem by means of the present invention, which is characterized in that one adds an amount of at least 0.2% by weight, preferably 0,5% by weight of a fatty acid, a fatty alcohol, and/or a fat to the mass of amino acid.

Further characteristics will be evident from the accompanying claims.

Among those amphoteric amino acids or amphoteric derivatives of amino acids which are most troublesome particularly acetyl cysteine, methyl dopa, L-dopa, carboxymethyl cysteine can be mentioned.

Among fats, fatty acids, and fatty alcohols particularly those are chosen having 14 to 20 C, whereby particularly cetanol, stearic acid, stearylic alcohol, hydrolyzed castor oil, Na-stearyl fumarate, Precirol ® (mono, di, and triesters of palmitinic and stearic acid with glycerin) can be mentioned.

An addition of at least 0.2% by weight of said compound to the mass of amino acid can be enough to prevent the fluidization problem. However, larger amounts may be added if so required, and if allowed without influencing the final use. Thus up to 20% by weight can be used.

The invention will be explained more in detail below with reference to the examples given.

EXAMPLE A

In a device for fluid bed treatment (NICASYSTEM ® FLUID-BED COATER) 200 g of crystalline acetyl cysteine were introduced. Fluidization was started by blowing in air. After 3 seconds the fluidization had come to a complete stop and the mass of acetyl cysteine had settled like a cake on the walls of the device.

EXAMPLE 1

In the same device as used in Example A 500 g of crystalline acetyl cysteine were introduced and the fluidization was started while simultaneously adding 5 g of cetanol dissolved in methylene chloride-isopropanol 50:50. The fluidization was not influenced, but further treatment of the crystalline acetyl cystein could take place during good fluidization conditions.

The particle size of the acetyl cysteine treated in this example was 0.8 mm.

Other solvents for the dissolution of the said compounds are acetone, ethanol, or mixtures of methylene chloride, acetone, isopropanol and ethanol.

I claim:

1. A process for treating amphoteric amino acids comprising:
   introducing an amphoteric amino acid mass of acetyl cysteine, methyl dopa, L-dopa, or carboxymethyl cysteine into a fluid bed and adding at least 0.2% by weight of amphoteric amino acid mass of cetanol, stearic acid, stearyl alcohol, hydrolyzed castor oil, Na-stearyl fumarate, mono-, di- or triesters of palmitinic acid with glycerin or mono-, di- or triesters of stearic acid with glycerin or a mixture thereof.

2. The process according to claim 1, wherein the amphoteric amino acid mass contains at least 80% by weight of acetyl cysteine, methyl dopa, L-dopa or carboxymethyl cysteine.

3. The process according to claim 1, wherein at least 2% by weight of cetanol, stearic acid, stearyl alcohol, hydrolyzed castor oil, Na-stearyl fumarate, or mono-, di- or triesters of palmitinic acid with glycerin or mono-, di- or triesters of stearic acid with glycerin or a mixture thereof is added.

4. Process according to claim 3, wherein cetanol is added.

5. Process according to claim 3, wherein stearylic alcohol is added.

6. Process according to claim 3, characterized in that stearic acid is added.

7. Process according to claim 1, wherein cetanol is added.

8. Process according to claim 1, wherein stearylic alcohol is added.

9. Process according to claim 1, characterized in that stearic acid is added.

10. Process according to claim 2, wherein the cetanol is added.

11. Process according to claim 2, wherein stearylic alcohol is added.

12. Process according to claim 2, characterized in that stearic acid is added.

13. The process of claim 1 wherein at least 0.5% by weight of amphoteric amino acid mass of cetanol, stearic acid, stearyl alcohol, hydrolyzed castor oil, Na-stearyl fumarate, mono-, di- or triesters of palmitinic acid with glycerin or mono-, di- or triesters of stearic acid with glycerin or a mixture thereof is added.

14. A process for treating acetyl cysteine comprising:
   introducing acetyl cysteine into a fluid bed, adding at least 0.2% by weight of acetyl cysteine of cetanol, stearic acid, stearylic alcohol or mixtures thereof to the acetyl cysteine, and fluidizing the acetyl cysteine.

15. The process of claim 14 wherein cetanol is added.

16. The process of claim 14 wherein stearylic alcohol is added.

17. The process of claim 14 wherein stearic acid is added.

* * * * *